US009155488B2

(12) United States Patent
Kapon et al.

(10) Patent No.: US 9,155,488 B2
(45) Date of Patent: *Oct. 13, 2015

(54) METHOD AND DEVICE FOR MONITORING BREASTFEEDING

(71) Applicant: Yeda Research and Development Co. Ltd., Rehovot (IL)

(72) Inventors: Ruti Kapon, Rehovot (IL); Arik Peled, Ramat-Gan (IL); Shahar Seifer, Mazkeret Batia (IL); Revital Schneider, Rishon-LeZion (IL)

(73) Assignees: Yeda Research and Development Co., LTd., Rehovot (IL); PELED Arik, Ramat-Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/975,400

(22) Filed: Aug. 26, 2013

(65) Prior Publication Data

US 2013/0338528 A1    Dec. 19, 2013

Related U.S. Application Data

(63) Continuation of application No. 12/863,604, filed as application No. PCT/IL2009/000085 on Jan. 21, 2009, now Pat. No. 8,521,272.

(60) Provisional application No. 61/053,069, filed on May 14, 2008, provisional application No. 61/006,558, filed on Jan. 22, 2008.

(51) Int. Cl.
*A61B 5/053* (2006.01)
*A61B 5/00* (2006.01)

(52) U.S. Cl.
CPC .............. *A61B 5/0531* (2013.01); *A61B 5/0535* (2013.01); *A61B 5/4288* (2013.01); *A61B 5/4312* (2013.01)

(58) Field of Classification Search
CPC .... A61B 5/053; A61B 5/0531; A61B 5/4312; A61B 5/4288
USPC .................................................. 600/547, 587
See application file for complete search history.

(56) References Cited

U.S. PATENT DOCUMENTS 6,125,297 A     9/2000    Siconolfi
6,314,315 B1    11/2001   Hung et al.
(Continued)

FOREIGN PATENT DOCUMENTS

WO    WO 2006/054287    5/2006
WO    WO 2007/067632    6/2007
(Continued)

OTHER PUBLICATIONS

Applicant-Initiated Interview Summary Dated Mar. 22, 2013 Re. U.S. Appl. No. 12/863,604.
(Continued)

*Primary Examiner* — Sean Dougherty
*Assistant Examiner* — Michael C Stout

(57) ABSTRACT

A method of monitoring amount of milk consumed by an infant being breastfed by a breast is disclosed. The method comprises: determining variations in electric capacitance of the breast during breastfeeding, and correlating the electric capacitance variations to an amount of milk consumed by the infant.

21 Claims, 11 Drawing Sheets

(56) References Cited

U.S. PATENT DOCUMENTS

| | | | |
|---|---|---|---|
| 7,043,296 B1* | 5/2006 | Kasai et al. | 600/547 |
| 7,499,745 B2 | 3/2009 | Littrup et al. | |
| 8,521,272 B2 | 8/2013 | Kapon et al. | |
| 2002/0022787 A1* | 2/2002 | Takehara et al. | 600/547 |
| 2005/0192511 A1 | 9/2005 | Shiokawa | |
| 2005/0203435 A1* | 9/2005 | Nakada | 600/547 |
| 2006/0111645 A1* | 5/2006 | Petrucelli | 600/547 |
| 2006/0247543 A1* | 11/2006 | Cornish et al. | 600/508 |
| 2008/0077042 A1* | 3/2008 | Feldkamp et al. | 600/547 |
| 2008/0319336 A1* | 12/2008 | Ward et al. | 600/547 |
| 2009/0076410 A1* | 3/2009 | Libbus et al. | 600/547 |
| 2009/0082679 A1* | 3/2009 | Chetham | 600/508 |
| 2009/0306535 A1* | 12/2009 | Davies et al. | 600/547 |
| 2009/0312666 A1 | 12/2009 | Fukumoto et al. | |
| 2010/0081960 A1* | 4/2010 | McKenna | 600/547 |
| 2010/0217148 A1* | 8/2010 | Binder | 600/547 |
| 2010/0292604 A1 | 11/2010 | Kapon et al. | |
| 2011/0082358 A1 | 4/2011 | Davies | |

FOREIGN PATENT DOCUMENTS

| | | |
|---|---|---|
| WO | WO 2009/060448 | 5/2009 |
| WO | WO 2009/093238 | 7/2009 |

OTHER PUBLICATIONS

International Preliminary Report on Patentability Dated Aug. 5, 2010 From the International Bureau of WIPO Re.: Application No. PCT/IL2009/000085.

International Search Report Dated May 25, 2009 From the International Searching Authority Re.: Application No. PC/LL2009/000085.

Notice of Allowance Dated Apr. 24, 2013 Re. U.S. Appl. No. 12/863,604.

Official Action Dated Dec. 12, 2012 Re. U.S. Appl. No. 12/863,604.

Official Action Dated May 17, 2012 Re. U.S. Appl. No. 12/863,604.

Patent Examination Report Dated Mar. 26, 2013 From the Australian Government, IP Australia Re. Application No. 2009207275.

Request for Examination Dated Jan. 23, 2013 From the ROSPATENT, Federal Government Institution, Federal Institute of Industrial Property of the Federal Service for Intellectual Property, Patents and Trademarks Re. Application No. 2010133254 and Its Summary in English.

Translation of Office Action Dated Dec. 22, 2011 From the State Intellectual Property Office of the People's Republic of China Re. Application No. 200980111451.X.

Translation of Office Action Dated Oct. 30, 2012 From the State Intellectual Property Office of the People's Republic of China Re. Application No. 200980111451.X.

Written Opinion Dated May 25, 2009 From the International Searching Authority Re.: Application No. PCT/IL2009/000085.

Macdonald "Impedance Spectroscopy", Annals of Biomedical Engineering, 20: 289-305, 1992.

Examination Report Dated Sep. 26, 2013 From the Instituto Mexicano de la Propiedad Industrial Re. Application No. MX/a/2010/007982 and Its Summary in English.

* cited by examiner

METHOD AND DEVICE FOR MONITORING BREASTFEEDING

RELATED APPLICATIONS

This Application is a continuation of U.S. patent application Ser. No. 12/863,604 filed on Jul. 20, 2010, which is a National Phase of PCT Patent Application No. PCT/IL2009/000085 having International filing date of Jan. 21, 2009, which claims the benefit of priority of U.S. Provisional Patent Application Nos. 61/053,069 filed on May 14, 2008, and 61/006,558, filed on Jan. 22, 2008. The contents of the above applications are all incorporated herein by reference.

FIELD AND BACKGROUND OF THE INVENTION

The present invention, in some embodiments thereof, relates to a breastfeeding and, more particularly, but not exclusively, to a method and device for monitoring breastfeeding by capacitance measurement.

It is recognized that breastfeeding is beneficial for newborns as well as mothers. Pediatricians and other health care providers promote breastfeeding as a normal part of daily life, and encourage mothers to continue breastfeeding for as long as mutually desired.

Breastfeeding is beneficial for newborns from the standpoint of general health, growth, development. In particular, breastfeeding significantly decreases the risk for a large number of acute and chronic diseases. For example, studies show that breastfed babies are less likely to get diarrhea, ear infections, respiratory infections, bacteremia, bacterial meningitis, botulism, necrotizing enterocolitis, and urinary tract infections. In addition, breastfeeding provide the baby with a sense of closeness, warmth and security.

Many studies indicate that breastfeeding is also beneficial to the mother. For example, statistically, breastfeeding mothers return to their normal weight more rapidly. Breastfeeding is also known as one of the factors that delay the resumption of ovulation, which may be beneficial for mothers or families who wish to increase child spacing.

Occasionally, the amount of mother milk consumed by breastfed babies is not sufficient. When a breastfed baby enters a stress condition, it is desired to monitor the amount of milk consumed by the breastfed baby so as to determine whether or not lack of feeding is one of the sources of the stress. Several techniques are known for monitoring breastfeeding.

The most widely employed technique is weight subtraction. In this technique, the baby's weight is measured before and after breastfeeding, and the amount of milk consumption is calculated by subtracting the two weights.

Another technique is disclosed in Daly et al., Exp. Physiology, 77, 79-87 (1992). In this technique, changes in breast volume are traced by photographing the breast before and after feeding.

U.S. Published Application No. 20058271913 and International Patent Publication No. WO 2006/054287 disclose a technique in which a volumetric flow sensor is placed inside a silicon nipple cap through which the baby suckles. The milk flow data from the sensor is converted into milk volume data which is displayed a display monitor.

International Patent Publication No. WO 2006/054287 discloses breastfeeding monitoring via Doppler-shift measurements. an ultra-sonic Doppler-effect transmitter and receiver probes positioned proximate to the nipple are activated during the breastfeeding session to measure the amount of flow through the nipple. The amount of flow is translated and accumulated into milk volume.

SUMMARY OF THE INVENTION

According to an aspect of some embodiments of the present invention there is provided a method of monitoring amount of milk consumed by an infant being breastfed by a breast. The method comprises: determining variations in electric capacitance of the breast during breastfeeding, and correlating the electric capacitance variations to an amount of milk consumed by the infant.

According to some embodiments of the invention the method further comprises measuring the electric capacitance so as to determine the variations.

According to some embodiments of the invention the measurement of the electric capacitance is performed so as to estimate electric capacitance of an interior of the breast while reducing contribution of a skin of the breast to the electric capacitance.

According to some embodiments of the invention the measurement of the electric capacitance comprises measuring a phase of voltage sampled from a skin of the breast in response to an electrical current applied to the skin.

According to some embodiments of the invention the phase is measured via at least four electrodes connected to a skin of the breast.

According to some embodiments of the invention the method further comprises correcting the correlation using history data collected during previous breastfeeding sessions.

According to some embodiments of the invention the method further comprises measuring electric resistance of the breast, and calculating a multiplication between the electric resistance and the electric capacitance, wherein the amount of milk is correlated to the multiplication.

According to some embodiments of the invention the method further comprises performing a calibration measurement prior to the breastfeeding so as to collect calibration data, wherein the multiplication is corrected based on the calibration data.

According to some embodiments of the invention the method further comprises using the multiplication for searching over the breast for regions occupied clusters of alveoli.

According to some embodiments of the invention the method further comprises subtracting contribution of a skin of the breast to the electric capacitance.

According to some embodiments of the invention the contribution of the skin to the electric capacitance and an overall electric capacitance of the breast are measured by different electrical circuitries.

According to some embodiments of the invention the method further comprises measuring a thickness of the skin, wherein the contribution of the skin to the electric capacitance is estimated based on the thickness.

According to some embodiments of the invention the electric capacitance is measured by a capacitance measuring device devoid of electrical contact with the skin.

According to some embodiments of the invention the electric capacitance is measured, at least partially, by at least one device selected from the group consisting of a capacitance bridge, an LCR meter and an oscillation frequency measuring device.

According to some embodiments of the invention the electric capacitance is measured via a plurality of electrodes, wherein the method employs at least one multiplexing cycle such that at different sub-cycles of the multiplexing cycle, a different set of electrodes is used for measuring the electric capacitance.

According to some embodiments of the invention the method further comprises using capacitance values measured during the at least one multiplexing cycle for determining a capacitance measuring locations on the breast in future sessions.

According to some embodiments of the invention the method further comprises analyzing capacitance values measured during the at least one multiplexing cycle so as to differentiate between measurement sensitivities in different depths in the breast.

According to an aspect of some embodiments of the present invention there is provided a breastfeeding monitor system. The system comprises a capacitance measuring unit adapted for measuring variations in electric capacitance of a breast during breastfeeding, and a processing unit for correlating the electric capacitance variations to an amount of milk consumed by an infant being breastfed by a breast.

According to some embodiments of the invention the capacitance measuring unit is configured for measuring electric capacitance of an interior of the breast, while reducing contribution of a skin of the breast to the electric capacitance.

According to some embodiments of the invention the capacitance measuring unit is configured for determining the capacitance based on a phase of a voltage sampled from a skin of the breast in response to an electrical current applied to the skin.

According to some embodiments of the invention the capacitance measuring unit comprises at least four electrodes connectable to a skin of the breast.

According to some embodiments of the invention the system further comprises a memory medium for storing history data collected in previous breastfeeding sessions, wherein the processing unit is configured for correcting the correlation using the history data.

According to some embodiments of the invention the system further comprises a resistance measuring unit for measuring electric resistance of the breast, wherein the processing unit is configured for calculating a multiplication between the electric resistance and the electric capacitance, wherein the amount of milk is correlated to on the multiplication.

According to some embodiments of the invention the processing unit is configured for correcting the multiplication based on calibration data collected prior to the breastfeeding.

According to some embodiments of the invention the electric resistance and the electric capacitance are measured at a plurality of frequencies, wherein the multiplication is performed for each of the plurality of frequencies, wherein the amount of milk is correlated to a combination of at least two multiplications.

According to some embodiments of the invention the processing unit is configured for subtracting contribution of a skin of the breast to the electric capacitance.

According to some embodiments of the invention the capacitance measuring unit comprises a skin capacitance measuring circuitry configured for measuring the contribution of the skin, and an overall capacitance measuring circuitry configured for measuring an overall electric capacitance of the breast.

According to some embodiments of the invention the system further comprises a skin thickness measuring device for measuring a thickness of the skin, wherein the processing unit is configured for estimating the contribution of the skin to the electric capacitance based on the thickness.

According to some embodiments of the invention the capacitance measuring unit is configured to measure the electrical capacitance while being electrically isolated from the skin of the breast.

According to some embodiments of the invention the capacitance measuring unit comprises at least one device selected from the group consisting of a capacitance bridge, an LCR meter and an oscillation frequency measuring device.

According to some embodiments of the invention the electric capacitance is measured at a frequency of less than 100 MHz.

According to some embodiments of the invention the electric capacitance is measured via a plurality of electrodes, wherein the system comprises a controller for employing at least one multiplexing cycle such that at different sub-cycles of the multiplexing cycle, a different set of electrodes is used for measuring the electric capacitance.

According to some embodiments of the invention the processing unit is configured for using capacitance values measured during the at least one multiplexing cycle so as to determine capacitance measuring locations on the breast in future sessions.

According to some embodiments of the invention the processing unit is configured for analyzing capacitance values measured during the at least one multiplexing cycle so as to differentiate between measurement sensitivities in different depths in the breast.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
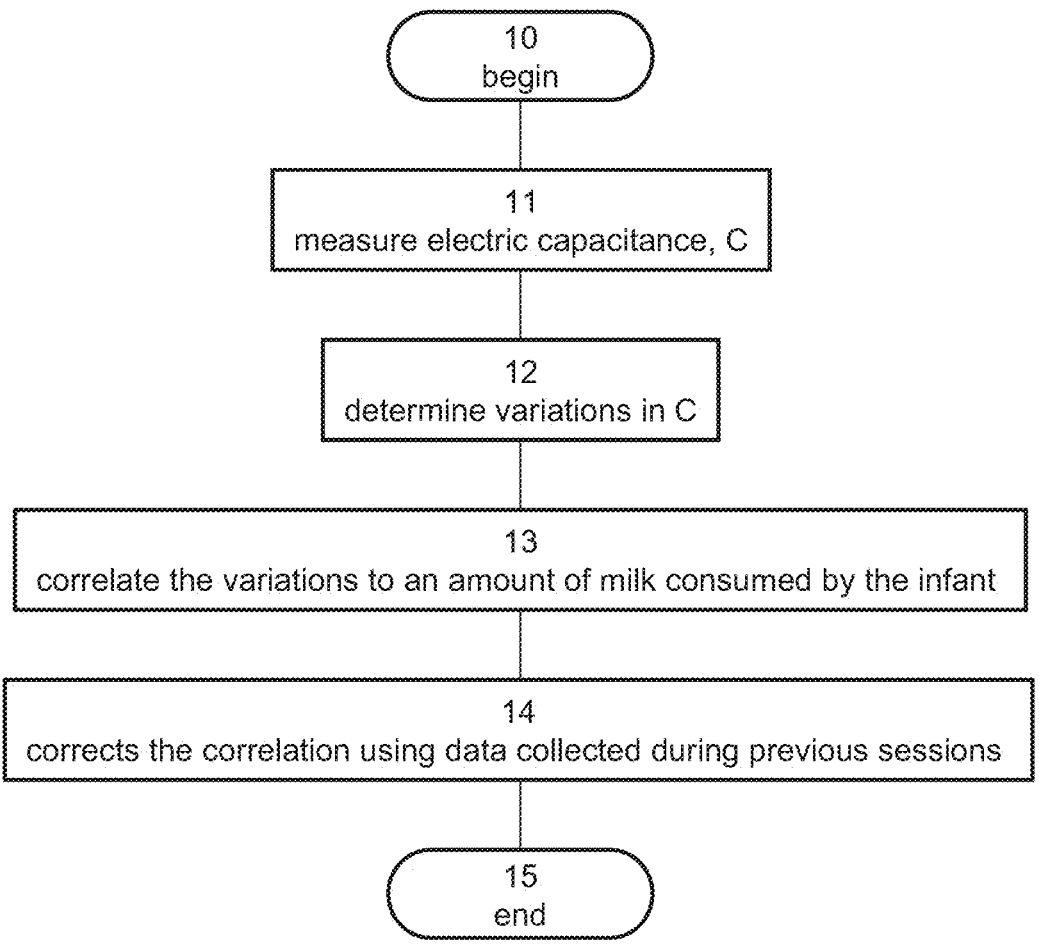
FIG. 1 is a flowchart diagram illustrating a method suitable for monitoring amount of milk consumed by an infant being breastfed by a breast, according to various exemplary embodiments of the present invention.

The present invention, in some embodiments thereof, relates to a breastfeeding and, more particularly, but not exclusively, to a method and device for monitoring breastfeeding by capacitance measurement.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors found that the amount of milk in the breast can be correlated to the electrical capacitance of the breast. It is recognized that the amount of milk before and after breastfeeding can be used for estimating the amount of milk consumed by an infant being breastfed by the breast. This is because the typical sucking rate of an infant is about 400 ml per hour, while the production rate of milk in a breast is typically less than 60 ml per hour (about 30 ml per hour on the average). Thus, the amount of milk differentiated over time with addition of the average production rate result in the estimated suckling rate within 7% error at maximal confidence.

The present inventors have therefore devised a technique for monitoring the amount of consumed milk, by measuring the electrical capacitance of the breast. The dependence of the amount of milk (volume or mass) on the electric capacitance of the breast according to the discovery of the present inventors will now be explained.

The milk is stored in the alveoli of the breast, which are small glands of about 0.1 mm diameter. During milk expression, the alveoli decrease in size. The membrane of each alveolus behaves as dielectric layer since it blocks ionic conductance. Under AC electric field, these membranes conduct displacement currents hence influence the capacitance of the breast. More specifically, average cross-section of the alveoli in random orientation can be sensed by measuring the breast's capacitance. It is recognized that the average cross-section of the alveoli is a proxy to their average volume, hence also to the volume of milk in the breast.

Without being bound to any theory it is predicted that the shape and size of the alveoli is approximately universal, since the milk is held in the alveoli only due to molecular force. The size of the alveoli is bound from above to prevent spontaneous milk draining, and from below to allow milk suctioning by a relatively low suction force. Under this approximation, the relation between the measured capacitance and milk volume is also universal.

There are two tissue types in the breast that contract during milk expression: the alveoli and myoepithelial cells. The myoepithelial cells surround the alveoli and contract in response to Oxytocin hormone to help depleting the milk. Yet, since the myoepithelial cells posse 1-6% of the breast volume, their contraction is expected to have negligible effect on the capacitance. The amount of milk in the ducts between the alveoli and the nipple store is about 10 ml, which is small compared to the alveoli that may store about 200 ml. Thus, to a good approximation, the dependence of the capacitance on the average alveolus volume can be considered linear. Additional considerations with respect to the relation between the capacitance and the average volume of the alveoli are provided in the Examples section that follows (see Example 1).

Figure 2:
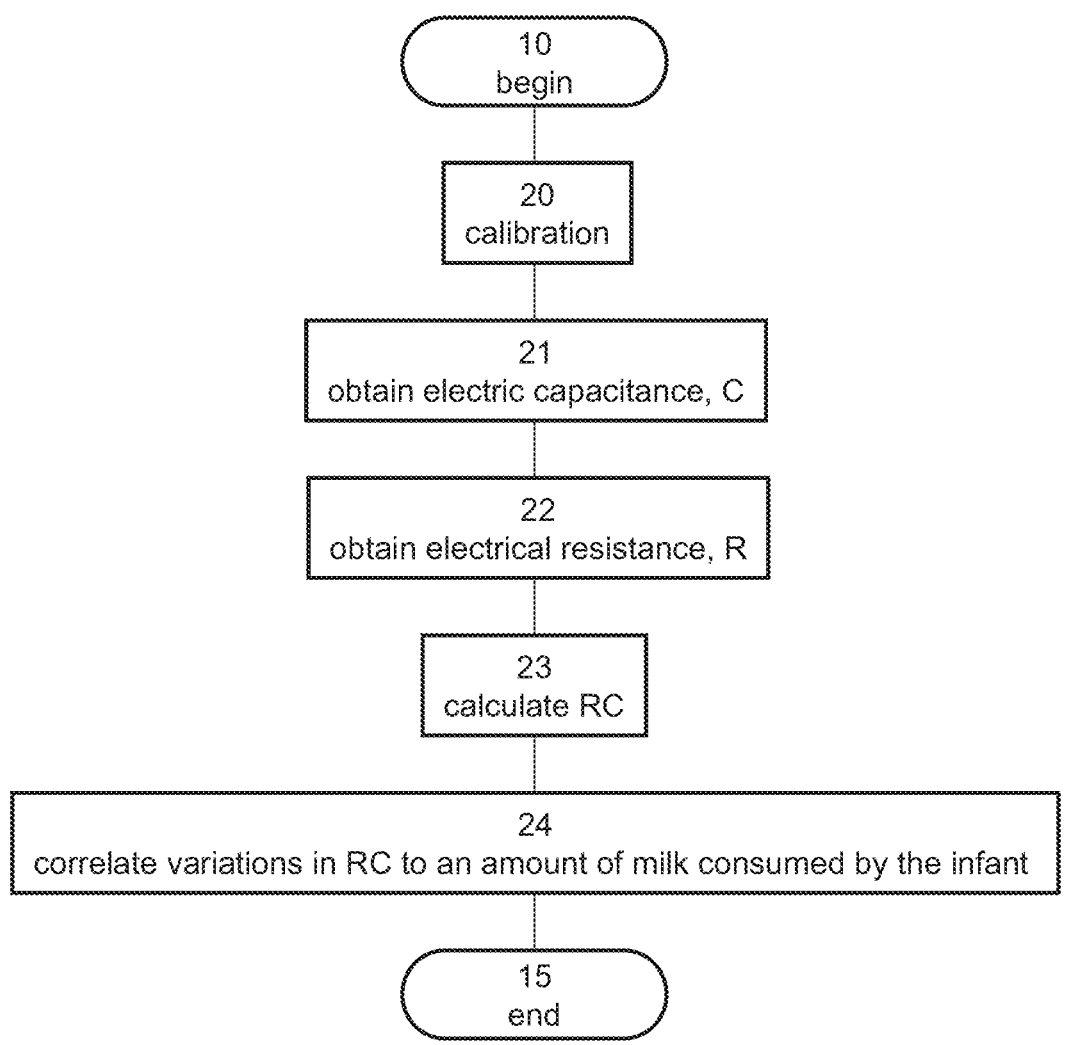
FIG. 2 is a flowchart diagram of the method in embodiments in which the amount of milk is correlated to the electric capacitance and the electric resistance of the breast.

Referring now to the drawings, FIGS. 1 and 2 are flowchart diagrams illustrating a method suitable for monitoring amount of milk consumed by an infant being breastfed by a breast, according to various exemplary embodiments of the present invention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more method steps, appearing in the following description or in the flowchart diagrams in a particular order, can be executed in a different order (e.g., a reverse order) or substantially contemporaneously. Additionally, several method steps described below are optional and may not be executed.

The method begins at 10 and optionally continues to 11 at which electric capacitance C of the breast is measured during breastfeeding. The capacitance can be measured using any measuring device known in the art. Preferred techniques for measuring the electric capacitance according to some embodiments of the present invention are provided hereinunder. In some embodiments, 11 is not executed. In these embodiments, the method preferably receives electrical capacitance data from an external source.

The method continues to 12 at which variations in the electric capacitance during the breastfeeding are determined. The method continues to 13 at which the variations in capacitance are correlated to an amount of milk consumed by the infant. In some embodiments of the present invention the method proceeds to 14 at which the correlation is corrected using history data collected during previous breastfeeding sessions. The history data can include capacitance data and/or milk amount data and/or data pertaining to intervals between successive sessions.

The history data can be used in more than one way. In some embodiments of the present invention history data is used for calibration. In some embodiments of the present invention average values collected on several sessions are used to improve the accuracy of the extracted milk amount over time. In some embodiments, history data are used for estimating the absolute content of the milk in the breast, for example, by comparing a contemporary value of capacitance or its descendants with the minimal capacitance in the history data. Optionally, the estimation is based, at least in part, on the intervals between successive sessions and/or the procedure employed for measuring the capacitance in the previous sessions (e.g., electrodes location, etc.).

The method ends at 15.

FIG. 2 is a flowchart diagram of the method in embodiments in which the amount of milk is correlated to the electric capacitance and the electric resistance of the breast. The method begins at 10 and continues to 21 at which the capacitance C is obtained and 22 at which an electric resistance R is obtained. The method can measure C and/or R directly or receive capacitance and/or resistance data from external sources. The method can then continue to 23 at which the method multiplies R by C and 24 at which the method determine variations in RC and correlates them to the amount of consumed milk. The advantage of using RC as a measure for estimating the amount of milk is that it is substantially invariant to changes in the shape of the breast that may occur during the breastfeeding session.

In some embodiments of the present invention the breastfeeding session is preceded by a calibration measurement, shown at 20, which is performed so as to collect calibration data. In these embodiments, the value of RC is corrected using the calibration data, and the amount of milk is correlated to the corrected value of RC. A preferred calibration procedure according to some embodiments of the present invention is provided hereinunder.

In some embodiments of the present invention the method corrects the correlation using history data (e.g., capacitance, resistance, milk amount, intervals between successive sessions) collected during previous breastfeeding sessions, as further detailed hereinabove.

The method ends at 15.

In various exemplary embodiments of the invention the measurement the capacitance is measured at a frequency which is less than 100 MHz, preferably from about 1 kHz to about 100 MHz, more preferably from about 1 KHz to about 10 MHz, more preferably from about 1 kHz to about 1 MHz or from about 1 kHz to about 100 kHz or from about 10 kHz to about 100 kHz. The advantage of this embodiment is that at low frequencies the breast intracellular liquid primarily conducts as ionic solution and not as dielectric matter, and the remaining dielectric matter resides in thin membranes inside the breast and at the skin.

In some embodiments of the present invention the measurement of electric capacitance is performed so as to determine the electric capacitance of the interior of the breast, while reducing or minimizing skin contribution to electric capacitance. The variation in capacitance of the internal breast tissue results from variations in the amount or shape of biological dielectric matter and is therefore better correlated to the amount of milk in the breast.

Following is a description of several techniques for measuring the capacitance of the breast, according to various exemplary embodiments of the present invention.

In some embodiments, the measurement includes transmission of electrical current through the skin and internal breast tissue and sampling of response voltage from the skin. This can be done via a plurality of electrodes connected to a skin of the breast. In these embodiments, the capacitance and optionally resistance of the breast is determined based on the phase of the sampled voltage.

Figure 3A:
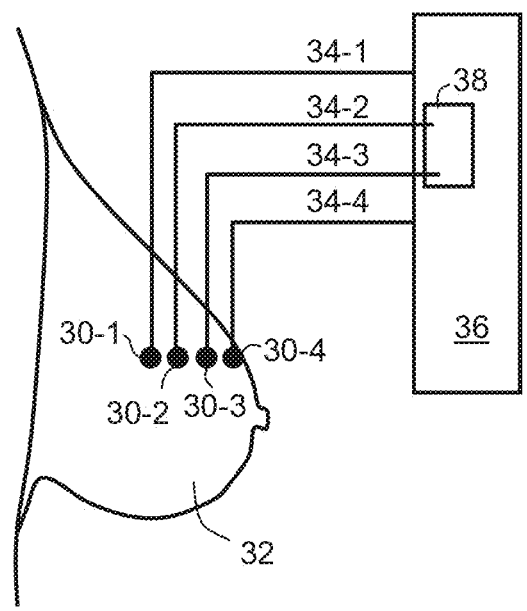
FIGS. 3A-B are schematic illustrations of an electrode configuration on a breast, according to various exemplary embodiments of the present invention.

FIG. 3 is a schematic illustration of a configuration which can be used according to some embodiments of the present invention for measuring the phase. FIG. 3 illustrates an embodiment in which a four-electrode configuration is employed, but it is to be understood that the number of electrodes can be other than four. In various exemplary embodiments of the invention at least four electrodes are employed.

Shown in FIG. 3 are four electrodes 30-1, 30-2, 30-3 and 30-4 attached to the skin of a breast 32 and in electrical communication with a capacitance measuring unit 36 via four wires 34-1, 34-2, 34-3 and 34-4, respectfully. The electrodes can be form on or integrated with a pad or a chip (not shown, see, e.g., FIG. 6) which can be attached to the skin or clipped to a breastfeeding brassier (e.g., to the strips of the brassier). A pressing mechanism such as arcs, foam or springs can be employed for press the electrodes against the skin.

One pair of the electrodes (say, electrodes 30-1 and 30-4) can serve as a current pair which applies AC current to the skin and another pair of the electrodes (say, electrodes 30-2 and 30-3) can serve as a voltage-pair which samples the voltage from the skin. The electrodes in the voltage pair are preferably buffered with an amplifier 38 which features high input impedance. Preferably, the input impedance of amplifier 38 is at least 100 MΩ or at least 1 GΩ, so as to ensure voltage sampling with minimal or without current.

A preferred location of the electrodes on the breast is the upper part of the breast, about 4-8 cm above the nipple. The advantage of selecting this location is that this part of the breast is generally planar and the geometry does not change significantly during milk expression. The electrodes can be arranged on pad (not shown, see FIG. 6) which can be made sticky to allow fast attachment of the electrodes to the skin.

The amplitude of the transmitted electrical current is preferably from about 0.05 mA to about 0.5 mA. The amplitude of the signal applied to the current pair can vary, depending on the quality of the electric contact between the electrodes and the skin. Generally, better electrical contact reduces the amplitude of the applied signal. For example, when bare and smooth conductive electrodes are used, a peak-to-peak amplitude of 1-5 volts can be applied to the current pair to generate the desired current.

The electric contact between the electrodes and the skin can be enhanced, thereby reducing the amplitude of the signal which generates the transmission current. Enhanced electrical contact can also facilitate sensing voltage from potential surfaces deep below the skin level, thereby allowing the present embodiments to measure the change in capacitance of the part of the breast tissue that contains milk alveoli. The electric contact can be enhanced using any contact enhancement technique known in the art.

In some embodiments of the present invention conductive electrode gel is employed. To this end a gel commonly used in electrocardiogram (ECG) electrodes can be used. This gel penetrates the stratum corneum of the skin (epidermis) and allows adequate electrical contact with the tissue below the skin. The contacting surface of the electrodes can be made, for example, from AgCl which reacts electrochemically with the gel and enhances the electrical current. This embodiment is particularly useful at low frequencies, e.g., below 20 KHz. In some embodiments of the present invention, electrode gel or hydrogel over metallic (e.g., stainless still) electrode surface is employed. The back of the electrode can include screen printed conductive layer. This embodiment is particularly useful at frequencies from about 20 kHz to about 1 MHz. The use of electrode gel is advantage also from the standpoint of measurement consistency since it reduces dependence of the penetrating current on the pressure of the electrode over the skin. When electrode gel is employed, a peak-to-peak amplitude of about 0.5 volts can be applied to the current pair to generate the desired current.

In some embodiments of the present invention the electrode surface includes conductive bulges or teeth. Once the surface is pressed on the skin, the capacitance of the skin is increased thereby facilitating better transmission of current to the tissue below the skin. Short teeth can penetrate the external dead layers of the skin (stratum corneum) and thus mimic the function of electrode gel without applying liquid or gel. When the electrode surface includes conductive bulges or teeth, a peak-to-peak amplitude of from about 0.5 volts to about 1 volt can be applied to the current pair to generate the desired current.

Figure 3B:
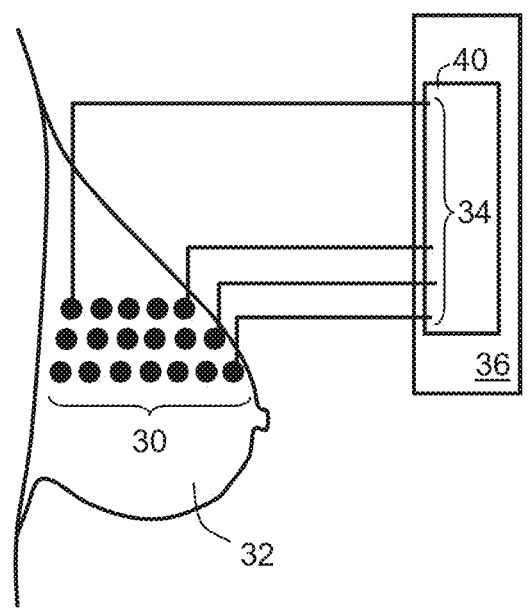
Figure 4:
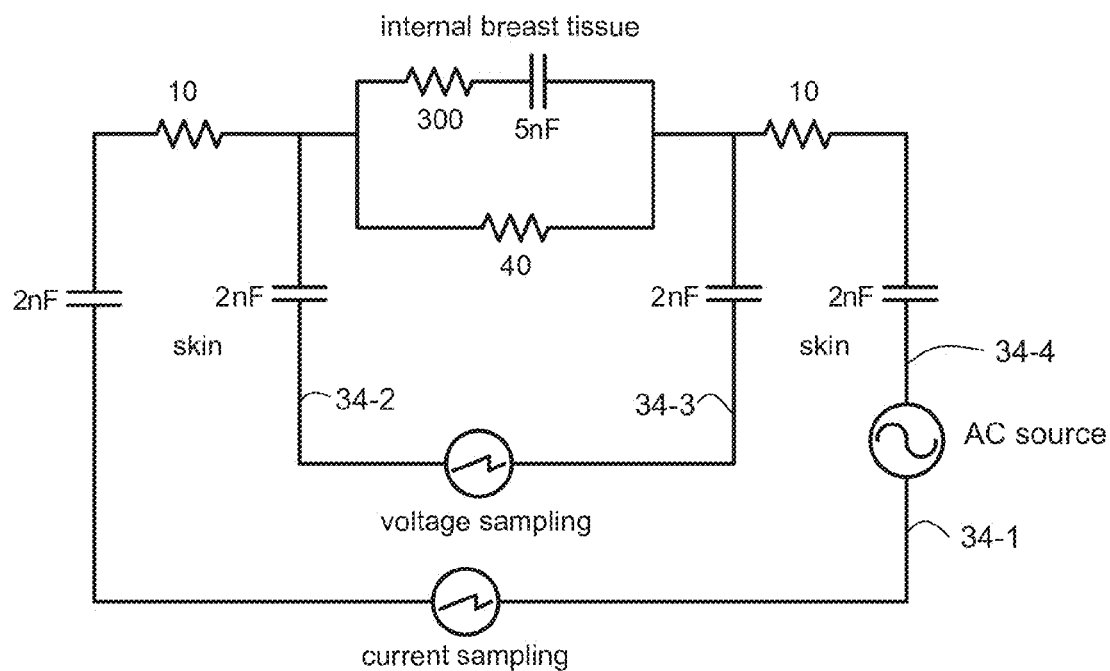
FIG. 4 is a schematic illustration of an electric analogue of the configuration in FIG. 3.
Figure 5:
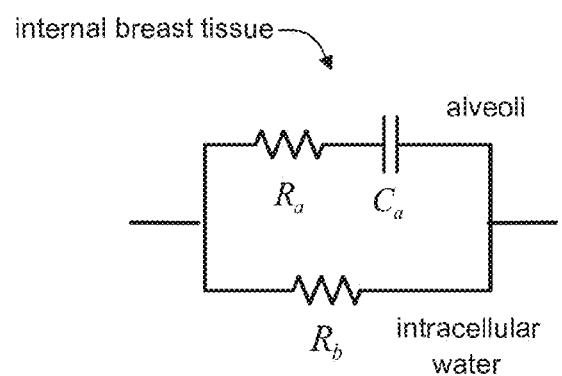
FIG. 5 is a schematic illustration of a 3 component electric analogue of internal breast tissue, according to various exemplary embodiments of the present invention.

The electric analogue of the configuration in FIG. 3 is illustrated in FIGS. 4 and 5. It is appreciated that FIGS. 4 and 5 are simplified circuits, which are not to be considered as limiting the scope of the present invention in any way. The values of the components in FIG. 4 indicate typical breast measurement results at frequencies of from about 10 to about 100 KHz, with ball electrodes pressed over the skin.

An AC generator transmits AC current via wires 34-1 and 34-4 through the skin to the internal breast tissue. The amplitude and phase of the transmitted current is sampled by a current sampling and measuring device. The amplitude and phase of the voltage of the internal breast tissue is sampled by voltage sampling and measuring device via wires 34-2 and 34-3. Without being bound to any specific theory, the internal tissue is modeled (see FIG. 5) as being equivalent to a resistor $R_b$ due to galvanic (ionic) conductivity via the intracellular water, and it is in parallel with a resistor $R_a$ and capacitor $C_a$ in series due to displacement conductance through the alveoli membranes. Passage of current through the internal tissue is modeled via low impedance (about 10Ω) conduction see FIG. 3). The skin is modeled as having much higher resistance than the tissue and high capacitance value.

The capacitance and optionally resistance of the internal breast tissue can be calculated using the sampled values of the voltage and current. Specifically, the capacitance can be calculated from the capacitive impedance $Z_{cap}$ defined as $i(\in/I)/\sin \Delta\phi$ using the relation $Z_{cap}=1/(i\omega C)$, where I is the applied current, $\in$ is the sampled voltage, $\Delta\phi$ is the phase difference between $\in$ and I, $i^2=-1$, $\omega=2\pi f$ and f is the frequency of the applied signal. In embodiment in which the amount of milk is correlated to R and C, the multiplication RC can be calculated using the relation:

$$\frac{|Z_{res}|}{|Z_{cap}|} = \left|\frac{R}{1/i\omega C}\right| = \omega RC,$$

where $Z_{res}$ is the measured resistive impedance defined as $(\in/I)/\cos \phi$.

Knowing the current also can be used to detect the pressure of dry electrodes on the skin. Resistance and capacitance slightly depend on the current and pressure of the electrodes on the skin. In a 4-wire measurement, the balance (difference between the sides) of the pressure between dry electrodes slightly modifies the capacitance results. The following procedure can be employed for tracing the balance. The current wires are temporarily switched. The current passes once between the rightmost couple of electrodes and once between the leftmost couple of electrodes and the two currents can be compared. If the currents are approximately the same (e.g., within 10%) then pressure can be considered balanced.

In embodiments in which the breastfeeding is preceded by a calibration measurement, the calibration can be expressed as a relation between C or RC and the parameters of the measurement. These parameters include, without limitation the current, I, the DC bias, $\in_{dc}$, and the balance between two sides of the electrodes construction, $I_1/I_2$, where $I_1$ is the current measured when signal is passed between, say, electrodes 30-1 and 30-2 and $I_2$ is the currents measured when signal is passed between, say, electrodes 30-3 and 30-4. For example, the calibration can include a fitting procedure, e.g., according to the relation:

$$C/C_0=(I/I_0)^{a_1}(\in_{dc}/\in_{dc0})^{a_2}(I_1/I_2)^{a_1}$$

where, $a_1$, $a_2$ and $a_3$ are fitted parameters and $C_0$, $I_0$ and $\in_{dc0}$ are average values during the calibration. Once $a_1$, $a_2$ and $a_3$ are fitted, breastfeeding can begin and the amount of milk can be correlated to the quantity $(I/I_0)^{a_1}(\in_{dc}/\in_{dc0})^{a_2}(I_1/I_2)^{a_1}RC$, referred to hereinunder as $(RC)_{comp}$. The parameters of the calibration are preferably selected so as to reduce the fluctuation of $(RC)_{comp}$ in terms of percent error.

In various exemplary embodiments of the invention the electric capacitance and optionally electric resistance are measured at a plurality of frequencies. In these embodiments, the signal which generates the transmitted electrical current is preferably a superposition of oscillating waveforms according to the number of frequencies that are sampled. The amount of milk can be estimated based on a combination of the measured values of C and optionally RC for each individual frequency.

For example, suppose without loss of generality that raw data are acquired at two frequencies, where for each frequency the data is expressed in terms of the resistance R and capacitance C as extracted from complex value current/and voltage $\in$ according to the relation:

$$\frac{I}{\varepsilon} = \frac{1}{R} + i\omega C.$$

On the other hand, in a 3-component electrical model of the breast (see FIG. 4) the components are interpreted via the relation:

$$\frac{I}{\varepsilon} = \frac{1}{R_b} + \frac{1}{1/i\omega C_a + R_a}.$$

Suppose further without loss of generality that the ratio between the two frequencies is 2. Denoting by R and C the values of the resistance and capacitance for the higher frequency, and by $R_{1/2}$ and $C_{1/2}$ the values of the resistance and capacitance for the lower frequency, useful measures can obtained using the following formulae:

$$R_a C_a = \frac{1}{\omega}\sqrt{-1 + 3/(4C/C_{1/2} - 1)},$$

and $$\frac{R_b}{R_a} = \left[\frac{4}{3\omega^2 R_a C_a}\left(\frac{1}{RC} - \frac{1}{R_{1/2}C_{1/2}}\right) - 1\right]^{-1}.$$

In experiments performed by the present inventors the ratio $R_b/R_a$ was found to be approximately proportional to RC. This ratio also approximates the ratio in cross sections of alveoli and the rest of the tissue and can therefore be used according to some embodiments of the present invention for searching over the breast for regions which are occupied with large clusters of alveoli compared to other regions.

In experiments performed by the present inventors it was found that the amount of milk can be correlated to the following quantity:

$$\frac{\Delta(R_{1/2}C_{1/2})}{\langle R_{1/2}C_{1/2}\rangle^{0.5}\langle R_a C_a\rangle^{0.4}(R_a C_a)^{0.1}},$$

where the symbol $\langle\rangle$ denotes average over history data ($R_a C_a$ and $R_{1/2}C_{1/2}$ in the present example) collected during several previous breastfeeding sessions, and the symbol $\Delta$ denotes a difference between the value of $R_{1/2}C_{1/2}$ that is measured before breastfeeding and the value of $R_{1/2}C_{1/2}$ that is measured after breastfeeding. In some embodiments of the present invention one or more of the history data averages is replaced with predetermined values.

The total amount of milk consumed by the infant can also be correlated to the following normalized change in capacitance:

$$\Delta C = \frac{C_1 - C_2}{C_1},$$

where $C_1$ is the capacitance before feeding and $C_2$ is the capacitance after feeding.

In some embodiments of the present invention two or more sets of electrodes (e.g., four or more electrodes per set) are attached to the breast, and multiplexing technique between the sets and between electrodes in the sets is employed for improving the accuracy of milk estimation. This embodiment is illustrated in FIG. 3B. A plurality of electrodes, generally shown at 30, contact breast 32 and are connected via a plurality of connection wires, generally shown at 34, to a controller 40 in unit 36. For clarity of presentation, FIG. 3B does not show a unique reference sign for each individual electrode and each individual connecting wire. Also only some of the connecting wires are depicted, but the skilled artisan would know how to connect the electrodes to controller 40 having a microprocessor therein.

Controller 40 is preferably configured for performing time-division multiplexing between the various electrodes. The multiplexing cycle comprises two or more sub-cycles wherein in each sub-cycle controller 40 selects a different set of electrodes, and unit 36 performs the measurement using the selected set of electrodes. In some embodiments of the present invention controller 40 selects four electrodes per sub-cycle. In these embodiment, unit 36 performs a four-wire measurement, as further detailed hereinabove, wherein two electrodes serve as a current pair for the respective sub-cycle and two electrodes serve a voltage pair for the respective sub-cycle.

The use of multiplexing reduces the effect of local disturbance (e.g., when an electrode is close to a blood vessel or another type of heterogeneity) on the measurement. Data acquisition from several sets of electrodes can also be used for determining a suitable location for attaching the electrodes in future sessions. This can be done, for example, by excluding locations at which the acquired data (e.g., values of RC or $R_b/R_a$) substantially deviate from the data acquired at other locations.

Multiplexing between various current and voltage electrode pairs can facilitate selective sensitivity to various depths in the breast tissue. Selective sensitivity can be based on various analysis principles, such as those used in Electrical Capacitance Tomography. Such analysis can be performed on the variations in capacitive impedance related to milk expression, acquired by the various electrode combinations. For example, values of $\Delta \log(C)$ (difference in capacitance logarithms before and after breastfeeding) of two or more electrode combination can be summed with appropriate sensitivity factors. The result can be a reconstructed value of $\Delta \log(C)$ at specific depth in the tissue. Thus, such technique allows picking a response from regions in the breast rich in milk alveoli and extracting their change in capacitance due to milk expression, in the same way a single impedance measurement is processed.

In some embodiments of the present invention an overall milk production rate is taken into consideration while correlating the measured quantities or combination of quantities to the amount of milk. This embodiment is particularly useful when the breastfeeding session is relatively long (e.g., above 30 minutes). The average rate of milk production (about 30 ml per hour) can be multiplied by the breastfeeding duration and added to the change in milk volume in the breast.

Figure 6:
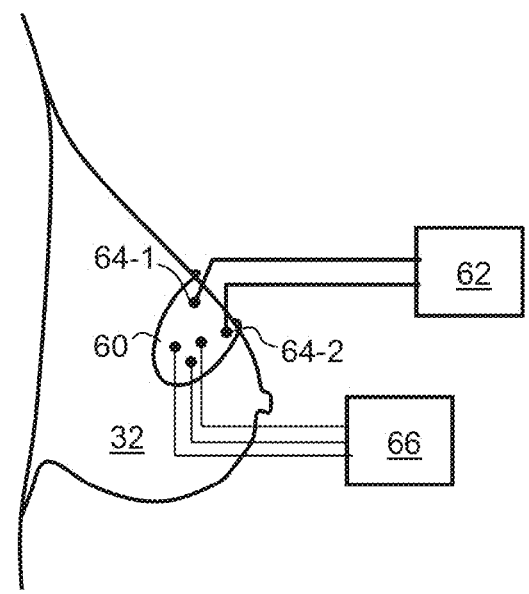
FIG. 6 is a schematic illustration of an embodiment of the present invention in which a pad is used for the measuring the capacitance.

FIG. 6 schematically illustrates an embodiment in which the capacitance measuring unit includes a pad 60 having therein two or more sensing electrodes 64-1 and 64-2 for sensing changes in the capacitance of breast 32. Electrodes 64-1 and 64-2 can be connected to a capacitance measuring circuitry 62, e.g., via a two-wire connection as shown. Although FIG. 6 shows an arrangement of two electrodes in pad 60, this need not necessarily be the case, since pad 60 can include more than two electrodes. Also, pad 60 can be connected to circuitry via any number of wires, which may be different from the number of electrodes in pad 60. For example, pad 60 can include four electrodes which are bridged in pairs and connected to circuitry 62 via a two-wire connection. One such configuration is similar to the configuration shown in FIG. 3 except that electrode 30-1 is bridged with electrode 30-2, and electrode 30-3 is bridged with electrode 30-4.

Pad 60 can be a sticky pad so as to facilitate the attachment of the pad to the breast. Also contemplated is a pad which comprises two detachable parts, wherein at the end of the breastfeeding session, one part of the pad is detached while the other part remains on the breast to mark the location for attaching the electrodes in the next session. At the beginning of the breastfeeding, the marker part of the pad can be detached to avoid interfering with the breastfeeding after the pad is in place.

Pad can also be made non-sticky. In this embodiment, pad 60 can be mounted on a breastfeeding brassier (e.g., to the strips of the brassier) or the like. The mounting is preferably such that the pad is pressed, e.g., by a pressing mechanism such as arcs, foam or springs, to the skin but with minimal or no deformation of the shape of the breast. For example, the pad and mounting mechanism can be made adjustable to the contour of the breast.

The electrodes in pad 60 can be in electrical contact with the skin or devoid of electrical contact with the skin, as desired. Configurations in which the electrodes are in contact with the skin are preferred from the standpoint of strong signal, while configurations without contact are preferred from the standpoint of comfort to the breastfeeding mother. It is appreciated that capacitance values measured without contacting the skin are less susceptible to current effects but are significantly lower compared to values measured by direct contact with the skin. Yet, it was found by the inventors of the present invention that non-contact configuration is sufficiently sensitive to changes in the shape of the breast, and can be therefore correlated to the amount of milk consumed by the infant.

Circuitry 62 is preferably sensitive to capacitance changes in the sub-picofarad range (e.g., 0.01-1 pF) when the sensing electrodes do not contact the skin, and in the nanofarad range (1-100 nF) when the sensing electrodes contact the skin. In some embodiments of the present invention circuitry 62 comprises a capacitance bridge, and in some embodiments circuitry 62 comprises an LCR meter. Also contemplated are embodiments in which circuitry 62 is an oscillation frequency measuring device, which detects oscillation frequency of a transistor or an amplifier using a feedback loop via one of the electrodes.

In some embodiments of the present invention the contribution of the skin to the electric capacitance is subtracted from the measured capacitance so as to isolate the capacitance of the internal breast tissue, which correlates better to the amount of milk.

The contribution of the skin to the electric capacitance can be measured in more than one way. In some embodiments, schematically shown in FIG. 6, the overall capacitance is measured by circuitry 62 and the skin capacitance is measured by a skin capacitance measuring circuitry 66 which is different from circuitry 62. Circuitry 66 can employ, for example, a 3-wire capacitance measuring technique, such as one of the techniques disclosed in Rosell et al, IEEE. trans. Biomed. Eng 35(8), 649 (1988), the contents of which are hereby incorporated by reference. In some embodiments, the contribution of skin to the electric capacitance is estimated based on the thickness of the skin. The thickness of the skin can be received as input from an external source, or it can be measured. Non-invasive techniques for measuring skin thickness are known in the art. In some embodiments, the thickness of the skin is measured by an oxymeter which emits infrared light in the direction of the skin and detects the reflected light intensity according to the distance from blood that scatters the light. The measured distance is the thickness of the dry skin layer.

Figure 7:
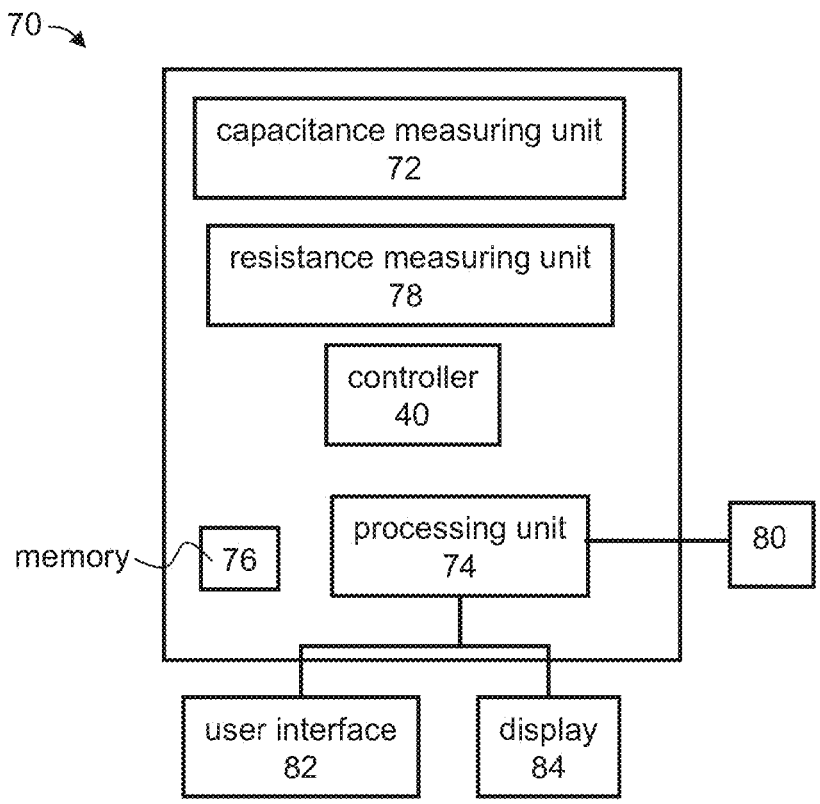
FIG. 7 is a schematic illustration of a breastfeeding monitor system, according to various exemplary embodiments of the present invention.

Reference is now made to FIG. 7 which is a schematic illustration of a breastfeeding monitor system 70, according to various exemplary embodiments of the present invention. System 70 can be used for execution any of the operations described above and in the flowchart diagrams of FIGS. 1 and 2.

System 70 comprises a capacitance measuring unit 72 adapted for measuring variations in the electric capacitance of the breast during breastfeeding, and a processing unit 74 for correlating the electric capacitance variations to the amount of milk consumed by the breastfed infant. Unit 74 is preferably a digital processing unit. Capacitance measuring unit 72 is preferably configured for measuring the electric capacitance of the interior of the breast, while reducing contribution of the skin to the electric capacitance. For example, unit 72 can comprise a plurality of electrodes connectable to the skin of the breast (not shown, see FIGS. 3 and 6) as further detailed hereinabove. In various exemplary embodiments of the invention unit 72 determines the capacitance based, at least in part, on the phase of the response voltage, as further detailed hereinabove. System 70 can further comprise a resistance measuring unit 78 which measures the electric resistance of the breast, as further detailed hereinabove. Processing unit 74 can calculate the multiplication RC and correlate the amount of milk to the value of RC, as further detailed hereinabove. In various exemplary embodiments of the invention system 70 comprises controller 40 which performs the time-division multiplexing between the various electrodes, as further detailed hereinabove.

Unit 74 can be configured to perform any of the above computational procedures for improving the accuracy of the correlation. Thus, for example, in some embodiments unit 74 combines measurements taken at different frequencies, in some embodiments unit 74 calculates the calibration factor, in some embodiments unit 74 corrects the correlation using history data collected in previous breastfeeding sessions, in some embodiments unit 74 analyses the measurements obtained in the various sub-cycles of the multiplexing cycle for determining suitable measuring locations in future sessions and/or for differentiating between measurement sensitivities in different depths in the breast, etc. In various exemplary embodiments of the invention system 70 comprises a memory medium 76 for storing the history data. Memory medium 76 is preferably a non-volatile memory medium.

In some embodiments of the present invention processing unit 74 is configured for subtracting the contribution of the skin to the electric capacitance. In these embodiment, capacitance measuring unit 72 preferably comprises a skin capacitance measuring circuitry and an overall capacitance measuring circuitry, as further detailed hereinabove. System 70 can further comprise a skin thickness measuring device 80 which measures the thickness of skin, as further detailed hereinabove. In this embodiment, processing unit 74 receives the value of the skin thickness from device 80 and estimates the contribution of the skin to the capacitance based on the thickness.

System 70 can also comprise a user interface module 82 and/a display device 84. User interface 84 can be configured to receive input from the user, e.g., regarding the initiation and termination of breastfeeding. Display device 84 can be a miniature display mounted in the same housing with unit 74. Display device 84 serves for displaying the monitoring results. The display can indicate the progress of milk expression during breastfeeding, for example, in the form of a graphical bar. At the final stage display device 84 can display the amount of consumed milk.

It is expected that during the life of a patent maturing from this application many relevant capacitance measuring techniques will be developed and the scope of the term capacitance measuring device is intended to include all such new technologies a priori.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Computational Model

In this example, additional considerations with respect to the relation between the capacitance and the average volume of the alveoli are provided, without being bound to any specific theory. The following is based on a computational model, which is not intended to limit the scope of the present invention in any way.

Figure 8:
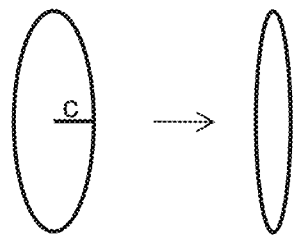
FIG. 8 is a schematic illustration describing an alveolus which collapses during expression of milk.

FIG. 8 is a schematic illustration describing a simplified alveolus which collapses during expression of milk. For clarity of presentation, the alveolus is presented as an oblate that collapses along the smaller axis c.

The average cross section of one oblate in random orientation can be calculated [Vickers and Brown Proc. R. Soc. Lond. A, 457, 283] as:

$$\langle \sigma_1 \rangle = \frac{\pi a^2}{2} + \frac{\pi a c}{2} \frac{\sinh^{-1} e}{e},$$

where e is the ellipticity of the oblate, defined as $e=(1-c^2/a^2)^{0.5}$ and a is half of the long diameter of the oblate (a>c). The right-most term of $\langle \sigma_1 \rangle$ is nearly a constant equals 0.88.

The volume of the oblate is:

$$V_1 = 4\pi a^2 c/3.$$

When the oblate is flattened a is approximately constant and the volume is proportional to c without noticeable change in oblate area (the surface of the oblate does not need to be elastic to accommodate the change in milk volume).

Assuming a uniform density of alveoli, n, the volume of the milk V can be related to the volume of the alveoli $V_1$:

$$V_1 = \frac{V}{nV_{breast}},$$

where $V_{breast}$ is the effective volume of the breast.

Figure 9:
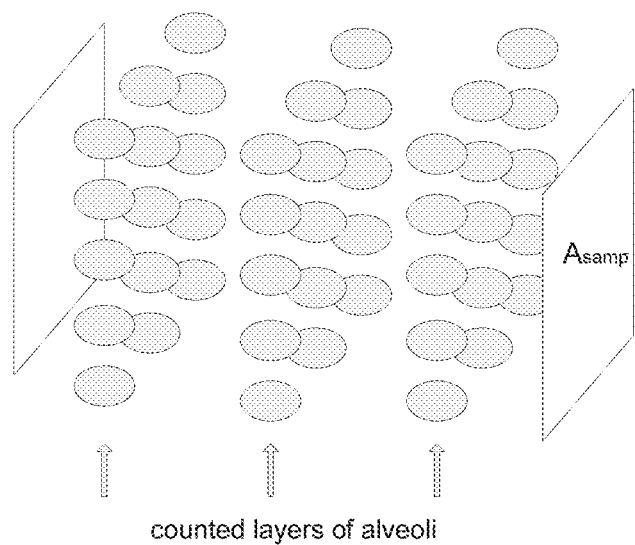
FIG. 9 is a schematic illustration describing an arrangement of alveoli according to a computational model employed by some embodiments of the present invention.

The capacitance of the numerous alveoli in the sampled volume can be assessed by counting the alveoli as if they are arranged in layers of a single alveolus in each position (see FIG. 9). Such a layer with area $A_{samp}$ defines the total cross section of the alveoli, $\langle \sigma \rangle$:

$$\langle \sigma \rangle = \langle \sigma_1 \rangle n^{2/3} A_{samp}$$

which can be written as:

$$\langle \sigma \rangle = \frac{\pi a^2}{2} n^{2/3} A_{samp} + \frac{0.88 \cdot 3}{8a} \frac{A_{samp}}{V_{breast}} n^{-1/3} V.$$

The total capacitance due to the alveoli is sampled between potential surfaces of separation distance $L_{samp}$:

$$C_{alv} = \frac{\varepsilon_0 \varepsilon_r \langle \sigma \rangle}{D_{eff}},$$

where $D_{eff}$ is the effective width of the entire insulting material between potential surfaces. Thus, in the present computational model all capacitance in series sum up to a single capacitor with effective thickness of insulting layer. Since in each layer of alveoli the cross section of insulting surface is 4 membranes of thickness d (two sides of the cell, at two sides of the alveolus that form its envelope), the total effective membrane can be calculated as:

$$D_{eff} = 4d(n^{1/3} L_{samp}).$$

Thus, the total capacitance can be written as:

$$C_{alv} = \left(\frac{A_{samp}}{L_{samp}}\right)\left(\frac{\varepsilon_0 \varepsilon_r}{d}\right) n^{1/3} \left[\frac{\pi a^2}{8} + \frac{0.88 \cdot 3}{32a} \frac{V}{N}\right],$$

where $N = nV_{breast}$ is the number of alveoli in the breast.

Without being bound to any theory, it can be assumed that on the average N, a and d have universal values for most women, otherwise breastfeeding would be either too hard for the infant to suck, or milk would express spontaneously. The density n, the amount of fat in the breast, and the shape of the breast may affect the value of C for a given milk volume V.

Example 2

Breastfeeding Monitoring Using a 4-Wire Configuration

Methods

Eleven lactating mothers participated in a total of 60 milk expression sessions, in which the mothers succeeded either to pump or to feed their baby with amount of more than 45 ml milk. The amount of milk was measured in the case of pumping according to the level of milk indicated in the bottle during several breaks of about ½ minute in the milk expression, and in the case of baby feeding according to the weight of the baby before and after eating. The accuracy of the former is 5 ml and of the latter is 10 ml. The density of pumped milk was tested regularly and can be assumed 1 gr/ml (with up to 7% error).

A 4-wire AC impedance method was used for monitoring. Four pediatric ECG electrodes (ConMed Huggables 1620-003) were placed in one line on the upper part of the breast at a constant location for each subject (±1 cm), 6-7 cm above the nipple. The inner voltage electrodes were separated by 65 mm and the outer current electrodes were placed further apart 30 mm from the voltage electrodes. The sampling signal was a waveform $0.5 \sin(\omega t) + 0.5 \sin(0.5 \omega t)$ in volts (t denotes time), where $\omega = 2\pi f$ and $f = 50$ kHz.

The waveform was generated with a National Instrument USB-6251 D/A output at an update rate of 2.5 MHz, and buffered through a INA117 differential amplifier. This oscillating voltage was connected to one electrode of the current pair, while the other electrode of the current pair was connected to ground via a 301 Ohm (0.1%) resistor that was used to sample the current according to the voltage difference on the resistor. The electrodes of the voltage pair were each amplified by a LT1793 JFet amplifier and sampled by the ND function of the NI USB-6251 acquisition card.

The sampled voltage $\in$ was based on the difference between the voltages on the two amplifier outputs. The sampled current and voltage were passed via Fast Fourier Transform (FFT) from a bank size of 1 second data at sampling rate of 1 MHz. The peaks at each tested frequency were located and the phase and amplitude of the Fourier transformed current and voltage were converted to resistance R and capacitance C in parallel model based on the equation:

$$\frac{I}{\varepsilon} = \frac{1}{R} + i\omega C$$

Results

Figure 11:
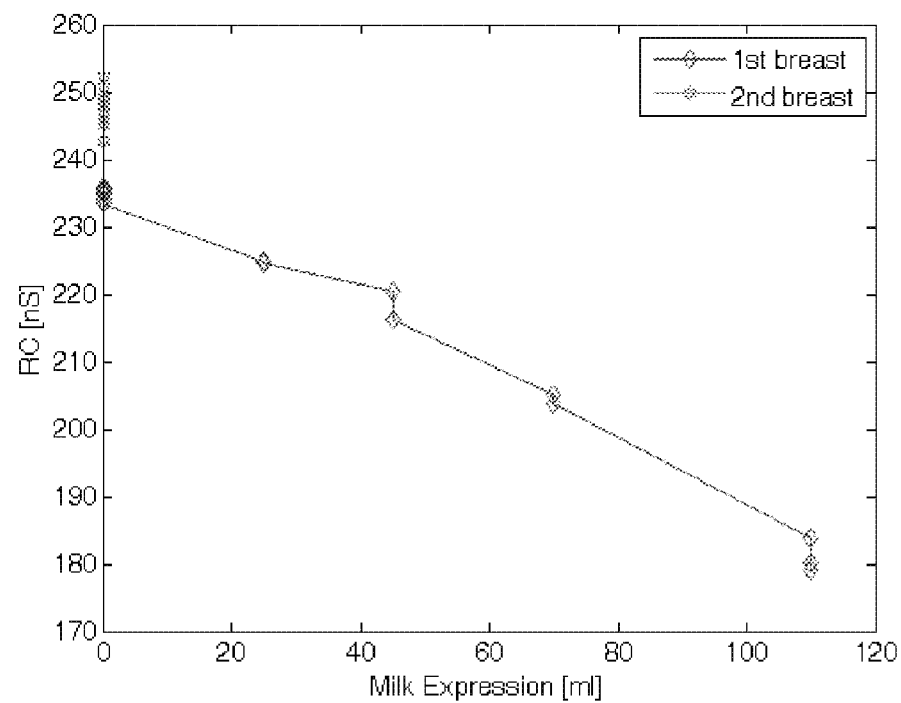
FIG. 11 shows a multiplication of resistance by capacitance as a function of the volume of consumed milk, as measured for a frequency of 50 kHz in experiments performed according to some embodiments of the present invention.
Figure 12:
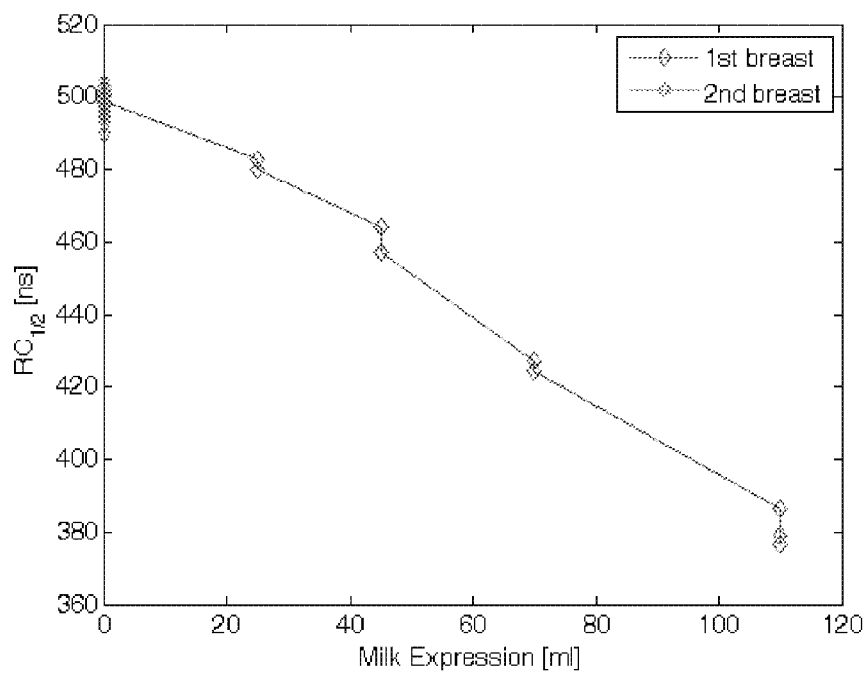
FIG. 12 shows a multiplication of resistance by capacitance as a function of the volume of consumed milk, as measured for a frequency of 25 kHz in experiments performed according to some embodiments of the present invention.
Figure 13:
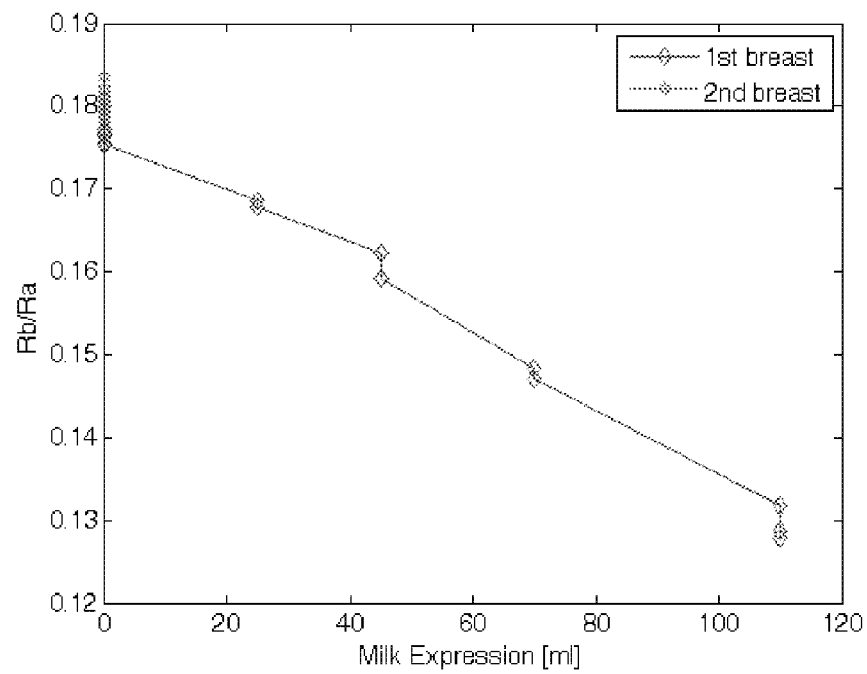
FIG. 13 shows a ratio of intracellular water resistance to alveoli resistance as a function of the volume of consumed milk, as measured in experiments performed according to some embodiments of the present invention.
Figures 14, 15:
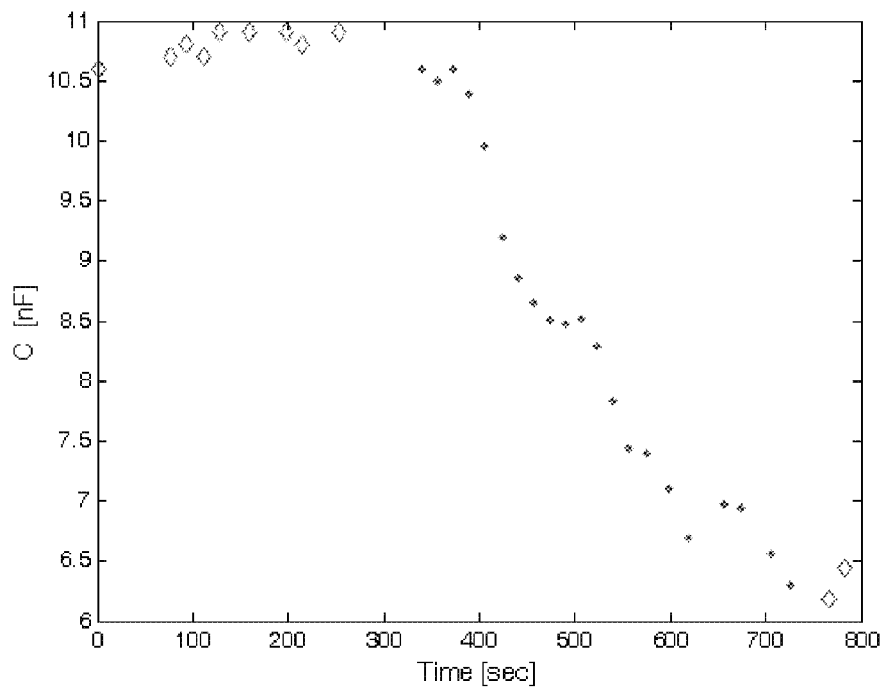
FIG. 14 shows capacitance as a function of time for a frequency of 50 kHz as measured in another set of experiments performed according to some embodiments of the present invention.
FIG. 15 shows the measured capacitance of FIG. 14 as a function of the volume of consumed milk.
Figure 16:
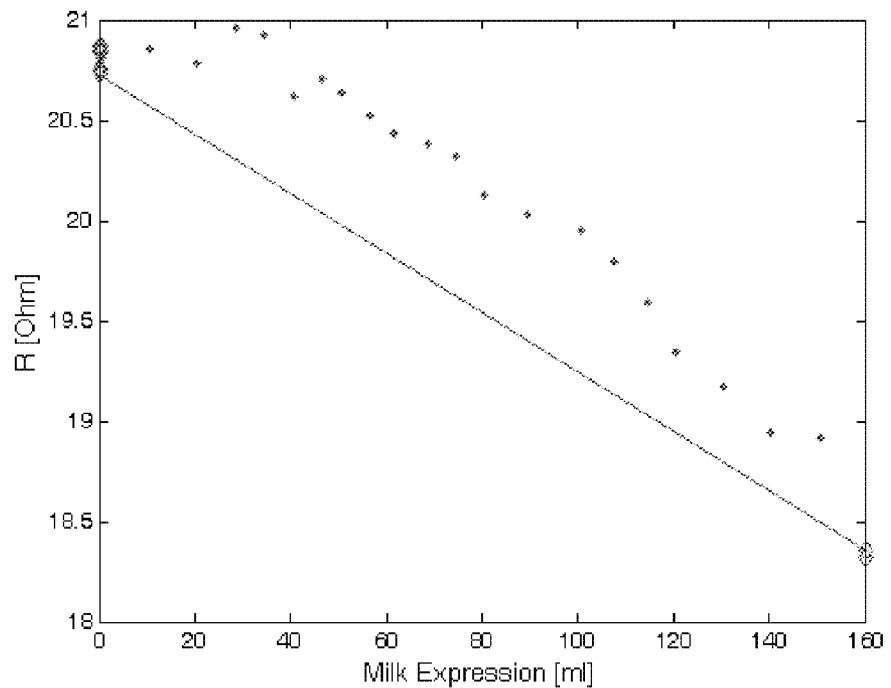
FIG. 16 shows resistance as a function of time for a frequency of 50 kHz as measured in experiments performed according to some embodiments of the present invention.

Results of the capacitance C, the multiplication RC for the higher frequency (50 kHz) and lower frequency (25 kHz), and the ratio $R_a/R_b$ as a function of the volume of consumed milk are shown in FIGS. 10-13, respectively, for one experimental session. C is expressed in nanofarads (FIG. 10), RC is expressed in nanoseconds (FIGS. 11 and 12) and the ratio $R_a/R_b$ is dimensionless (FIG. 13). The volume of consumed milk is expressed in milliliters. Results of another experimental session on a different subject are shown in FIGS. 14-16 (performed at 50 KHz frequency).

In the representative experimental session depicted in FIGS. 11-13, the following protocol was used: 5 minutes rest (i.e., no pumping or breastfeeding), 10 minutes pumping (from the 6th minute to the 15th minute), 4 minutes rest (from the 16th minute to the 19th minute), 5 minutes breastfeeding (from the 20th minute to the 24th minute) and 2 minutes rest (from the 25th minute to the 26th minute). 70 ml were pumped during the pumping period and 40 ml were breastfed during the breastfeeding period. The other breast was also monitored during the entire 26 minutes but did not express milk.

Each point in FIGS. 10-13 is based on an average of consecutive 10 samples of R and C, and the standard deviation of C was calculated from the 10 samples. Points with standard deviation of more than 2% of the average were discarded. The stability was about 0.2-1%. The slopes of RC as a function of the volume of consumed milk (FIGS. 11 and 12) were calculated based on the 2 lasts points immediately before starting milk expression and from the first 2 points immediately after stopping the milk expression. The slopes were followed in order to find a scaling between the volume of milk expressed and the electrical measurements.

Figure 10:
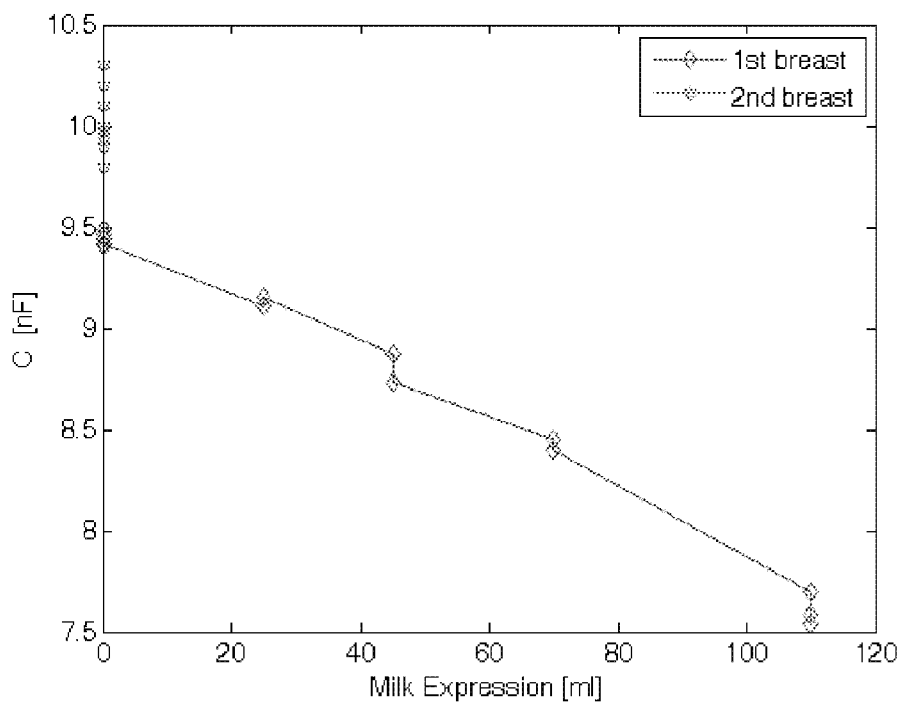
FIG. 10 shows capacitance in nanofarads as a function of the volume of consumed milk in milliliters, as measured in experiments performed according to some embodiments of the present invention.

The capacitance shows a decrease from an initial value of 9.5 nF to 7.7 nF owing to depletion of milk from the alveoli in the breast (FIG. 10). Linear dependence of the multiplication RC was observed for both the higher (FIG. 11) and lower (FIG. 12) frequencies. Similar behavior was observed in all other sessions. The slope $\Delta(RC)_{1/2}/\Delta V$ in this representative session is about −1.05 ns/ml. The value of $R_aC_a$ varied only slightly during the entire session ($R_aC_a$=4520±80 ns).

Results of an additional experimental session are presented in FIGS. 14-16. FIGS. 14-15 show variation of capacitance versus time and versus milk expression during breastfeeding, and FIG. 16 shows the variation of resistance. In FIGS. 14-16, diamonds designate measurements before and after the baby touched the breast, whereas dots designate measurements when the baby sucked from the breast (the location of the latter along the axis of milk expression assumes constant feeding rate). The seizing of the baby on the breast modifies the geometry and thus the capacitance and resistance are modified; however, the resistance increases and the capacitance decreases compared to the line between the stable measurements, so in values of RC the interruption by the seizing of the baby should decrease. Note that during expression of 160 ml the value of capacitance decreases by more than 40% while the change in resistance is much smaller in relative number (in other experimental sessions the variation of resistance is not correlated with milk expression).

Discussion

The standard deviation of the slopes $\Delta(RC)_{1/2}/\Delta V$ extracted from 60 sessions was found to be about 25% of the average slope value. When $\Delta(RC)_{1/2}$ was corrected using history data the slopes showed a decrease in the standard deviation to about 23.5% of the average. The following formula was used for correcting $\Delta(RC)_{1/2}$.

$$\frac{\Delta(RC)_{1/2}}{\langle R_{1/2}C_{1/2}\rangle^{0.5}\langle R_aC_a\rangle^{0.4}(R_aC_a)^{0.1}}$$

Figure 17:
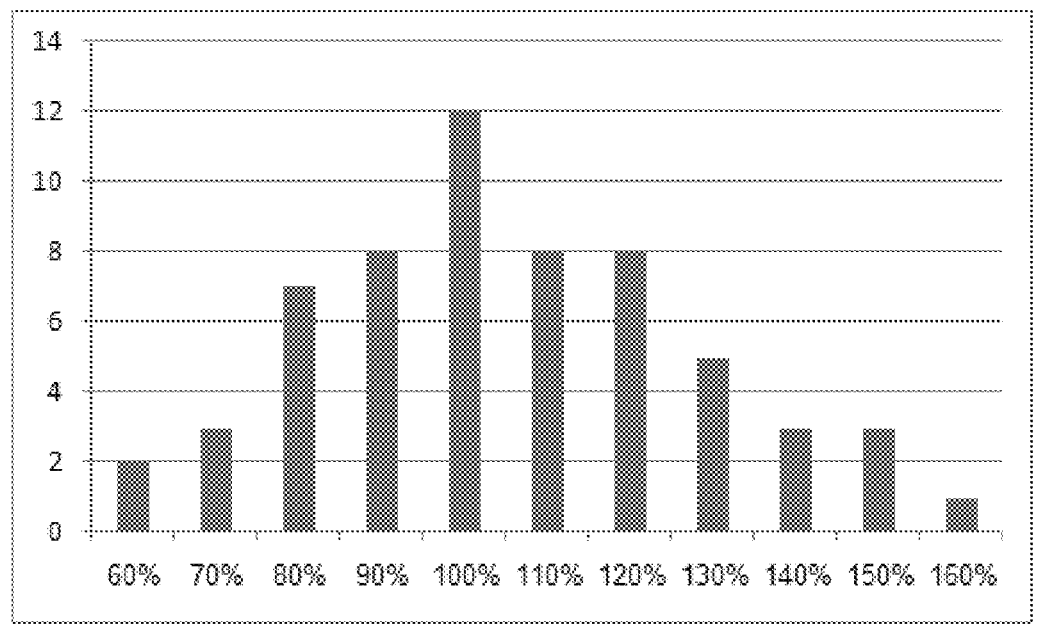
FIG. 17 is a histogram of experimental results obtained after employing a correction procedure, according to various exemplary embodiments of the present invention.

FIG. 17 is a histogram of the slopes after the correction, where the average slope is scaled to 100%. 72% of the values are within 20% error in the slope relative to the average.

The difference in percents relative to 100% can be interpreted as the error in predicting the change in milk volume based on electrical measurements with the given setup. The average value of the slope after correction can be used to determine change of milk volume using the setup as a monitor for breastfeeding.

The present experiment demonstrated that given the average slope, the measurement in accordance with some embodiments of the present invention of the difference in $\Delta(RC)_{1/2}$ and the initial values of $R_aC_a$ and $(RC)_{1/2}$ allows to predict the volume of consumed milk with an accuracy of 23.5% for any woman.

Example 3

Breastfeeding Monitoring Using a Non-Contacting Configuration

The amount of milk consumed by a baby during breastfeeding was monitored by measuring the capacitance between two electrodes placed on the breast but not in electrical contact with them during breastfeeding session.

Figure 18:
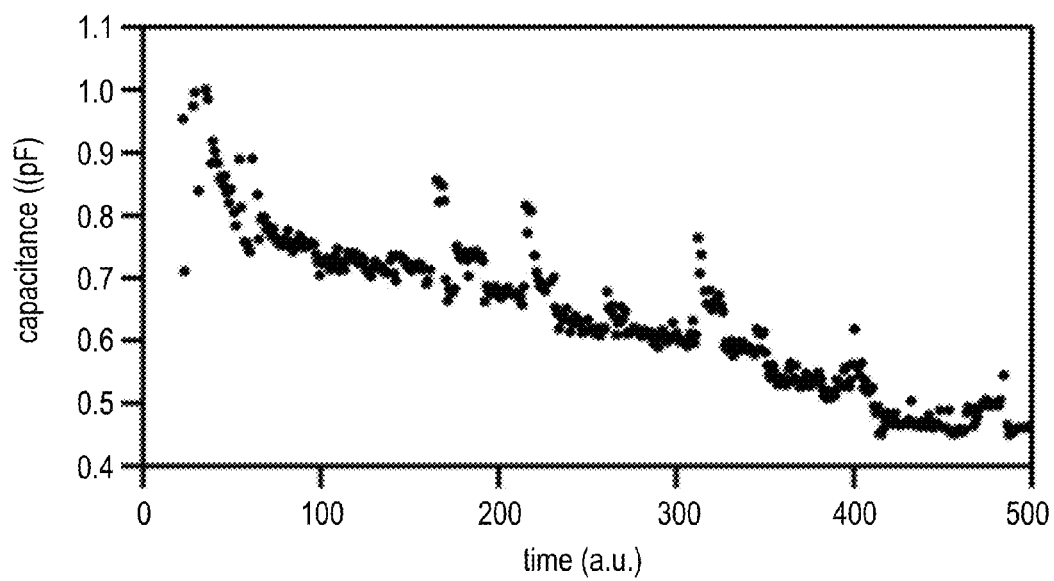
FIG. 18 shows a raw capacitance signal as a function of the time as measured in experiments performed according to some embodiments of the present invention.
Figure 19:
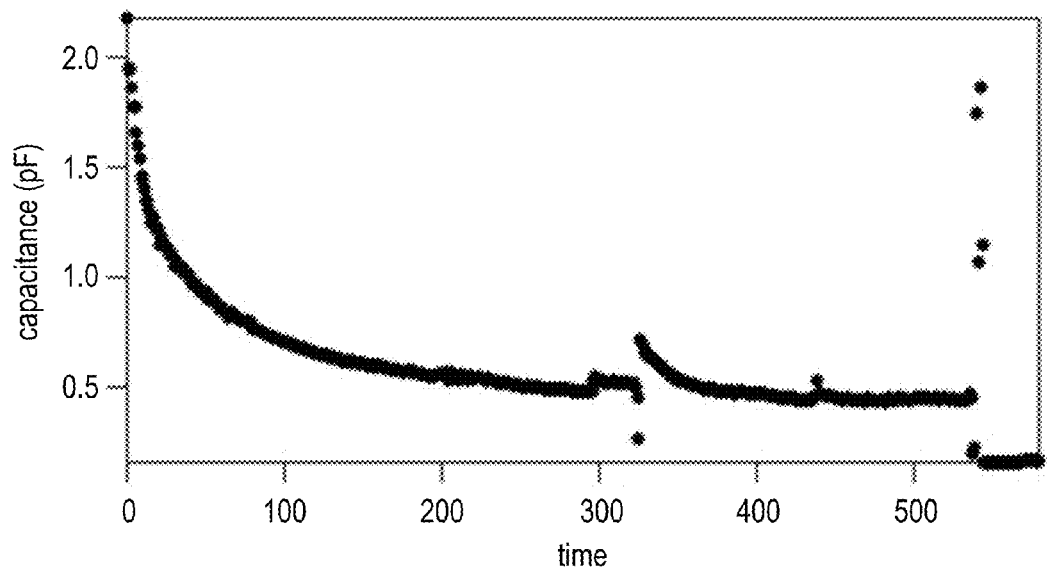
FIG. 19 shows a raw capacitance signal as a function of the time as measured in another set of experiments performed according to some embodiments of the present invention.

FIG. 18 and FIG. 19 show raw data of the capacitance signal in pF as a function of the time in arbitrary unit during one breastfeeding session. A continuous change in the capacitance was observed during the entire session. The observed change in capacitance is interpreted as a proxy to the amount of milk consumed by the baby during breastfeeding.

The amount of consumed milk can be correlated to the following normalized change in capacitance:

$$\Delta C = \frac{C_1 - C_2}{C_1},$$

where $C_1$ is the capacitance before feeding and $C_2$ is the capacitance after feeding.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A breastfeeding monitor system, comprising:
a measuring unit having a circuit, a plurality of electrodes and a skin conductivity enhancement material, wherein said circuit is configured for measuring a multiplication between electric resistance of a breast and electric capacitance of the breast during breastfeeding, and
a processing unit having circuit configured for determining variations in said multiplication and correlating said variations in said multiplication to an amount of milk consumed by an infant being breastfed by a breast.

2. The system of claim 1, wherein at least one of said electrodes comprises conductive bulges.

3. The system of claim 1, further comprising a housing, wherein said processing unit is mounted on said housing.

4. The system of claim 3, further comprising a miniature display device mounted on said housing.

5. The system of claim 3, wherein said processing unit is configured to display, using said display device, a total amount of consumed milk during a breastfeeding session.

6. The system of claim 3, wherein said processing unit is configured to display a progress of milk expression during breastfeeding using said display device.

7. The system of claim 3, wherein said processing unit is configured to display an amount of milk in said breast.

8. The system of claim 1, wherein said measuring unit is configured for determining said multiplication based on a phase of a voltage sampled from a skin of the breast in response to an electrical current applied to said skin.

9. The system of claim 1, wherein said measuring unit is configured for determining said multiplication based on a phase of a voltage over the skin of the breast in relation to an electrical current sampled entering said skin.

10. The system of claim 8, wherein said plurality of electrodes comprises at least four electrodes.

11. The system of claim 1, further comprising a memory medium for storing history data collected in previous breastfeeding sessions, wherein said processing unit is configured for correcting said correlation using said history data.

12. The system of claim 1, wherein said skin conductivity enhancement material is a conductive fluid or a conductive gel.

13. A method of monitoring amount of milk consumed during a breastfeeding session, the method comprising:
placing on the breast a plurality of electrodes and a skin conductivity enhancement material;

using a circuit for measuring a multiplication between electric resistance of the breast and electric capacitance of a breast during breastfeeding, and using a circuit for determining variations in said multiplication and correlating said variations in said multiplication to an amount of milk consumed by an infant being breastfed by a breast.

14. The method of claim 13, wherein at least one of said electrodes comprises conductive bulges.

15. The method of claim 13, wherein said circuit for determining said variations is mounted on a housing, and the method comprises displaying a total amount of consumed milk during the breastfeeding session using a miniature display device mounted on said housing.

16. The method of claim 15, further comprising displaying, using said display device, a total amount of consumed milk during the breastfeeding session.

17. The method of claim 15, further comprising displaying, using said display device, a progress of milk expression during breastfeeding.

18. The method of claim 15, further comprising displaying, using said display device, an amount of milk in said breast.

19. The method of claim 13, wherein said determining said multiplication is based on a phase of a voltage over the skin of the breast in relation to an electrical current entering said breast.

20. The method of claim 19, wherein said plurality of comprises at least four electrodes.

21. The method of claim 13, further comprising storing history data collected in previous breastfeeding sessions in a memory medium, wherein said correlation is corrected using said history data.

* * * * *